United States Patent [19]

Grollier et al.

[11] 4,184,844
[45] Jan. 22, 1980

[54] STORAGE STABLE INDOANILINE AND INDOPHENOL DYE SOLUTIONS, A PROCESS FOR PRODUCING THE SAME AND HAIR DYE COMPOSITIONS CONTAINING THE SAME

[75] Inventors: Jean F. Grollier; Chantal Fourcadier, both of Paris, France

[73] Assignee: L'Oreal, Paris, France

[21] Appl. No.: 816,499

[22] Filed: Jul. 18, 1977

[30] Foreign Application Priority Data

Jul. 21, 1976 [LU] Luxembourg ............................ 75425

[51] Int. Cl.$^2$ ............................ A61K 7/12; D06P 1/32
[52] U.S. Cl. .............................................. 8/10.2; 8/11
[58] Field of Search ............................................ 8/10.2

[56] References Cited

U.S. PATENT DOCUMENTS 3,960,476   6/1976   Ghilardi et al. ......................... 8/10.2

FOREIGN PATENT DOCUMENTS

| 44-21880 | 9/1969 | Japan | 8/10.2 |
| 744438 | 2/1956 | United Kingdom | 8/10.2 |
| 749045 | 5/1956 | United Kingdom | 8/10.2 |
| 1144100 | 3/1969 | United Kingdom | 8/10.2 |

Primary Examiner—Frederick E. Waddell
Attorney, Agent, or Firm—Cushman, Darby & Cushman

[57] ABSTRACT

A storage stable dye solution for use in coloring hair comprises a solution in an anhydrous solvent of at least one indophenol or indoaniline dye. These storage stable dye solutions at the time of dyeing the hair are admixed with an aqueous based cosmetic carrier conventionally employed in the hair dyeing art to provide a hair dye composition which is then immediately applied to the hair using conventional procedures.

8 Claims, No Drawings

STORAGE STABLE INDOANILINE AND INDOPHENOL DYE SOLUTIONS, A PROCESS FOR PRODUCING THE SAME AND HAIR DYE COMPOSITIONS CONTAINING THE SAME

The present invention relates to storage stable dye solutions wherein the dye is an indoaniline or an indophenol. The invention more particularly relates to a process for improving the storage stability of these dyes in a liquid medium prior to their ultimate use in an aqueous dye composition for coloring keratinic fibers and in particular living human hair.

BACKGROUND OF THE INVENTION

Indoaniline and indophenol dyes are well known and are disclosed for instance in commonly owned U.S. Pat. Nos. 4,007,747; 3,984,402; 3,977,825; 3,963,764; 3,929,404; 3,929,403; 3,894,837; 3,884,625 and 3,867,094. It has been observed, however, that full commercial exploitation of these dyes for coloring hair has been somewhat hindered principally because these dyes when stored in aqueous systems conventionally employed in the hair dyeing industry lack storage stability characteristics.

Storage stability is commercially of great significance because often compositions are stored for long periods of time, even as long as a few years, and often under elevated ambient temperature conditions.

Heretofore, in an effort to improve the storage stability of these dyes, it was proposed to employ them, not in the form of a previously prepared dye solution as had been done with dye compositions based on oxidation dyes, but rather in the form an anhydrous powder which was solubilized in an appropriate carrier immediately prior to application of the resulting dye composition to the hair.

While it would appear that this procedure not only solved the storage stability problem but also provided a way to achieve reproducible dyeings, nonetheless this procedure had its disadvantages in that the powdered dye did not dissolve as rapidly or as completely as desired or anticipated, at least in certain solvents or cosmetic vehicles. Thus the resulting dye compositions did not, at times, exhibit all the desirable characteristics.

In a subsequent effort to overcome these disadvantages, it was proposed to prepare these dyes in a form which was more rapidly soluble in conventional cosmetic vehicles or carriers. Thus, the dyes were transformed into lyophilizates or spray dried particles.

However, the dyes in these forms also exhibited disadvantages in that the lyophilization or spray dry operations employed to produce them are costly. Further the resulting lyophilizates and atomzates require a storage environment which is essentially humidity-proof. Moreover, rapid solubilization of the dyes in these forms required a significant amount of the solvent.

GENERAL DESCRIPTION OF THE INVENTION

It has now been discovered that the storage stability of indoanilines and indophenols can be improved and hence their dyeing power preserved, or at least not appreciably diminished during storage if these dyes are stored as solutions, in particular, anhydrous alcohols or monoalkyl ethers of ethylene glycol.

DETAILED DESCRIPTION OF THE INVENTION

Specifically, the present invention relates to a storage stable dye solution for use in coloring hair comprising a solution in an anhydrous solvent selected from the group consisting of ethyl alcohol, isopropyl alcohol, tertiobutyl alcohol, monomethyl ether of ethylene glycol, monoethyl ether of ethylene glycol, monobutyl ether of ethylene glycol and their mixtures, of at least one dye having the formula:

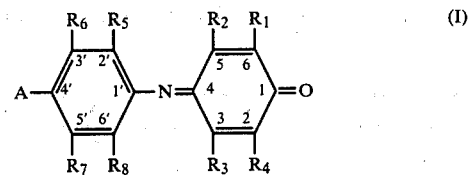

In one embodiment of the present invention, a given dye of Formula I can have one of the sets of values for substituents A, $R_9$, $R_{10}$, $R_5$, $R_6$, $R_7$ and $R_8$, tabulated below:

| A | $R_9$ | $R_{10}$ | $R_5$ | $R_6$ | $R_7$ | $R_8$ |
|---|---|---|---|---|---|---|
| OH | | | H | H | H | H |
| OH | | | Cl | H | H | H |
| OH | | | $CH_3$ | H | H | H |
| OH | | | H | Cl | H | H |
| OH | | | H | $CH_3$ | H | H |
| N$<^{R_9}_{R_{10}}$ | H | H | H | Cl | H | H |
| N$<^{R_9}_{R_{10}}$ | H | $C_2H_5$ | H | Cl | H | H |
| N$<^{R_9}_{R_{10}}$ | H | $CH_2CH_2OH$ | H | Cl | H | H |
| N$<^{R_9}_{R_{10}}$ | $CH_2CH_2OH$ | $CH_2CH_2OH$ | H | H | H | H |
| N$<^{R_9}_{R_{10}}$ | $CH_3$ | $CH_3$ | $CH_3$ | H | H | H |
| N$<^{R_9}_{R_{10}}$ | $C_2H_5$ | $CH_2CONH_2$ | $CH_3$ | H | H | H |
| N$<^{R_9}_{R_{10}}$ | $C_2H_5$ | $(CH_2)_2NHSO_2CH_3$ | $CH_3$ | H | H | H |
| N$<^{R_9}_{R_{10}}$ | $CH_3$ | $CH_3$ | H | Cl | H | H | while, with any one of these sets of values, the dye can also have one of the sets of values for substituents $R_1$, $R_2$, $R_3$ and $R_4$ tabulated below:

| $R_1$ | $R_2$ | $R_3$ | $R_4$ |
|---|---|---|---|
| $CH_3$ | H | $CH_3$ | H |
| $CH_3$ | H | H | $CH_3$ |
| $CH_3$ | H | $NH_2$ | H |
| $CH_3$ | H | $NH_2$ | $CH_3$ |
| $CH_3$ | H | $NHCOCH_3$ | H |
| $CH_3$ | H | $NHCOCH_3$ | $CH_3$ |
| $CH_3$ | H | $NHCONH_2$ | H |
| $OCH_3$ | H | $NHCOCH_3$ | H |

In another embodiment of the invention, a given dye of formula I can have one of the sets of values for substituents A, $R_9$, $R_{10}$, $R_5$, $R_6$, $R_7$ and $R_8$ tabulated below:

| A | $R_9$ | $R_{10}$ | $R_5$ | $R_6$ | $R_7$ | $R_8$ |
|---|---|---|---|---|---|---|
| $-N(R_9)(R_{10})$ | H | H | $CH_3$ | $OCH_3$ | H | $CH_3$ |
| $-N(R_9)(R_{10})$ | H | H | H | $CH_3$ | H | $CH_3$ | while, with any one of these sets of values, the dye can also have one of the sets of values for $R_1$, $R_2$, $R_3$ and $R_4$ tabulated below:

| $R_1$ | $R_2$ | $R_3$ | $R_4$ |
|---|---|---|---|
| $CH_3$ | H | $NH_2$ | H or $CH_3$ |
| $CH_3$ | H | $NHCOCH_3$ | $CH_3$ |
| $CH_3$ | H | $NHCONH_2$ | H |
| $OCH_3$ | H | $NHCOCH_3$ | H |

In yet another embodiment of the invention, a given dye of formula I can have one of the sets of values for substituents A, $R_9$, $R_{10}$, $R_5$, $R_6$, $R_7$ and $R_8$ tabulated below:

| A | $R_9$ | $R_{10}$ | $R_5$ | $R_6$ | $R_7$ | $R_8$ |
|---|---|---|---|---|---|---|
| $-N(R_9)(R_{10})$ | H | $CH_3$ | H | Cl | H | H |
| $-N(R_9)(R_{10})$ | $C_2H_5$ | $CH_2CONH_2$ | H | H | H | H |
| $-N(R_9)(R_{10})$ | $C_2H_5$ | $(CH_2)_2NHSO_2CH_3$ | H | H | H | H | while, with any one of these sets of values, the dye can also have one of the sets of values for substituents $R_1$, $R_2$, $R_3$ and $R_4$ tabulated below:

| $R_1$ | $R_2$ | $R_3$ | $R_4$ |
|---|---|---|---|
| $CH_3$ | H | $CH_3$ | H |
| $CH_3$ | H | H | $CH_3$ |
| $CH_3$ | H | $NH_2$ | H |
| $CH_3$ | H | $NH_2$ | $CH_3$ |
| $CH_3$ | H | $NHCOCH_3$ | $CH_3$ |
| $CH_3$ | H | $NHCONH_2$ | H |
| $OCH_3$ | H | $NHCOCH_3$ | H |

In still another embodiment of the present invention, a given dye of formula I can have one of the sets of values for substituents A, $R_9$, $R_{10}$, $R_5$, $R_6$, $R_7$ and $R_8$ tabulated below:

| A | $R_9$ | $R_{10}$ | $R_5$ | $R_6$ | $R_7$ | $R_8$ |
|---|---|---|---|---|---|---|
| $-N(R_9)(R_{10})$ | $CH_2CH_2OH$ | $CH_2CH_2OH$ | H | H | H | H |
| $-N(R_9)(R_{10})$ | $CH_3$ | $CH_3$ | $CH_3$ | H | H | H |
| $-N(R_9)(R_{10})$ | $CH_3$ | $CH_3$ | H | Cl | H | H |
| $-N(R_9)(R_{10})$ | $C_2H_5$ | $CH_2CONH_2$ | $CH_3$ | H | H | H |
| $-N(R_9)(R_{10})$ | $C_2H_5$ | $CH_2CONH_2$ | H | H | H | H |
| $-N(R_9)(R_{10})$ | $C_2H_5$ | $(CH_2)_2NHSO_2CH_3$ | $CH_3$ | H | H | H |
| $-N(R_9)(R_{10})$ | $C_2H_5$ | $(CH_2)_2NHSO_2CH_3$ | H | H | H | H | while, with any one of these sets of values, the substituents $R_1$, $R_2$, $R_3$ and $R_4$ have the following meanings: $R_1$ is methyl, $R_2$ is hydrogen, $R_3$ is $-NHCOOC_2H_5$ and $R_4$ is hydrogen.

These dyes can be prepared in accordance with known procedures such as those set forth in the above enumerated U.S. patents.

As a representative example, the dyes can be prepared by condensing a base, such as a paraphenylene diamine or a para amino phenol, on a coupler such as a phenol or a meta amino phenol in an aqueous medium, at a pH equal to or greater than 8, in the presence of an oxidizing agent such as potassium ferricyanide, potassium persulfate or $H_2O_2$.

It is also possible to prepare these dyes from a quinone imine corresponding to the paraphenylene diamine and para amino phenol and condensing this quonone imine on the coupler mentioned above.

Alternatively these dyes can be prepared from a nitroso derivative of the base, principally from tertiary paraphenylene diamines, and condesning this para nitroso derivative on the said coupler.

The most particularly preferred compounds in accordance with the present invention are prepared by combining a base selected from: para-amino phenol, 3-chloro-4-amino phenol, 3-methyl-4-amino phenol, 2-methyl-4-amino phenol, 2-chloro-4-amino phenol, 2,6-dimethyl-3-methoxy paraphenylene diamine, 2,5- dimethyl paraphenylene diamine, 2-chloro paraphenylene diamine, 3-methyl-4-amino N,N(ethyl, carbamylmethyl) aniline, 3-methyl-4-amino N,N-(ethyl, mesylaminoethyl) aniline, 4-amino N,N-(ethyl, carbamylmethyl) aniline, 4-amino N,N-(ethyl, mesylaminoethyl) aniline, 4-amino N,N-(di-β-hydroxyethyl) aniline, 3-chloro-4-methylamino aniline, 4-dimethylamino-2-methyl aniline, 4-dimethylamino-3-chloro aniline, 3-chloro-4-ethylamino aniline, 3-chloro-4-N,β-hydroxyethylamino aniline and a coupler selected from: 2-methyl-5-amino phenol, 2,6-dimethyl-3-amino phenol, 2,6-dimethyl-3-acetylamino phenol, 2-methyl-5-ureido phenol and 2-methoxy-5-acetylamino phenol.

Other compounds includable in the definition of the present invention and useful in the exploitation thereof are:

N-[(4'-hydroxy)phenyl]-3-acetylamino-6-methyl benzoquinone imine,
N-[(4'-hydroxy-2'-chloro)phenyl]-3-acetylamino-6-methyl benzoquinone imine,
N-[(4'-hydroxy-2'-methyl)phenyl]-3-acetylamino-6-methyl benzoquinone imine,
N-[(4'-hydroxy-3'-methyl)phenyl]-3-acetylamino-6-methyl benzoquinone imine,
N-[(4'-hydroxy-3'-chloro)phenyl]-3-acetylamino-6-methyl benzoquinone imine,
N-[(4'-amino-3'-chloro)phenyl]-3-acetylamino-6-methyl benzoquinone imine,
N-[[4'-N,N-(ethyl, carbamylmethyl)amino-2'-methyl]phenyl]-3-acetylamino-6-methyl benzoquinone imine,
N-[[4'-N,N-(ethyl, mesylaminoethyl)amino-2'-methyl]phenyl]-3-acetylamino-6-methyl benzoquinone imine,
N-[[4'-N,N-(di-β-hydroxyethyl)amino]phenyl]-3-acetylamino-6-methyl benzoquinone imine,
N-[(4'-N,N-dimethylamino-2'-methyl)phenyl]-3-acetylamino-6-methyl benzoquinone imine,
N-[(4'-N,N-dimethylamino-3'-chloro)phenyl]-3-acetylamino-6-methyl benzoquinone imine,
N-[(4'-N-ethylamino-3'-chloro)phenyl]-3-acetylamino-6-methyl benzoquinone imine and
N-[(4'-N-β-hydroxyethylamino-3'-chloro)phenyl]-3-acetylamino-6-methyl benzoquinone imine.

Other dyes usefully employed in the composition of the present invention include:

N-[[4'-N,N-(ethyl, carbamylethyl)amino]phenyl]-3-carbethoxyamino-6-methoxy benzoquinone imine,
N-[(4'-hydroxy-2'-chloro)phenyl]-3-ureido-6-methoxy benzoquinone imine,
N-[(4'-methylamino-3'-chloro)phenyl]-3-ureido-6-methoxy benzoquinone imine and
N-[[4'-N,N-(ethyl, carbamylmethyl)amino-3'-methyl]phenyl]-3-carbethoxyamino-6-methoxy benzoquinone imine.

The most particularly preferred storage stable dye solutions of the present invention are those which are solutions in ethyl alcohol, isopropyl alcohol, tertiobutyl alcohol, the monomethyl ether of ethylene glycol, monoethyl ether of ethylene glycol and monobutyl ether of ethylene glycol, of the following dyes:

N-[(4'-amino-3'-methoxy-2',6'-dimethyl)phenyl]-2,6-dimethyl-3-acetylamino benzoquinone imine,
N-[(4'-β-hydroxyethylamino-3'-chloro)phenyl]-6-methyl-3-ureido benzoquinone imine,
N-[[4'-N,N(ethyl, carbamyl methyl)amino]phenyl]-6-methyl-3-carbethoxyamino benzoquinone imine,
N-[(4'-methylamino-3'-chloro)phenyl]-6-methyl-3-ureido benzoquinone imine,
N-[(4'-methylamino-3'-chloro)phenyl]-2,6-dimethyl-3-acetylamino benzoquinone imine,
N-[(4'-hydroxy-2'-chloro)phenyl]-2,6-dimethyl-3-acetylamino benzoquinone imine,
N-[(4'-hydroxy-2'-chloro)phenyl]-6-methyl-3-ureido benzoquinone imine,
N-[[4'-N,N-(ethyl, carbamylmethyl)amino-2'-methyl]phenyl]-6-methyl-3-acetylamino benzoquinone imine,
N-[[4'-N,N-(ethyl, carbamylmethyl)amino-2'-methyl]phenyl]-6-methyl-3-ureido benzoquinone imine,
N-[[4'-N,N-(ethyl, carbamylmethyl)amino]phenyl]-2,6-dimethyl-3-acetylamino benzoquinone imine,
N-[(4'-amino-3'-chloro)phenyl]-2,6-dimethyl-3-acetylamino benzoquinone imine,
N-[(4'-amino-3',6'-dimethyl)phenyl]-6-methyl-3-ureido benzoquinone imine,
N-[[4'-N,N-(ethyl, mesylamino)amino-2'-methyl]phenyl]-3-amino-6-methyl benzoquinone imine,
N-[[4'-N,N-(ethyl, mesylamino)amino]phenyl]-2,6-dimethyl-3-acetylamino benzoquinone imine,
N-[(4'-hydroxy)phenyl]-3-acetylamino-6-methyl benzoquinone imine,
N-[(4'-amino-3'-chloro)phenyl]-3-acetylamino-6-methoxy benzoquinone imine,
N-[(4'-hydroxy)phenyl]-3-amino-6-methyl benzoquinone imine,
N-[[4'-N,N(ethyl, carbamylmethyl)amino]phenyl]-3-carbethoxy amino-6-methoxy benzoquinone imine,
N-[(4'-hydroxy-2'-chloro)phenyl]-3-ureido-6-methoxy benzoquinone imine,
N-[(4'-hydroxy-2'-chloro)phenyl]-3-acetylamino-6-methoxy benzoquinone imine,
N-[[4'-N,N-(ethyl, carbamylmethyl)amino]phenyl]-3-ureido-6-methyl benzoquinone imine,
N-[[4'-N,N-(ethyl, carbamylmethyl)amino]phenyl]-3-acetylamino-6-methoxy benzoquinone imine,
N-[(4'-hydroxy)phenyl]-3-acetylamino-2,6-dimethyl benzoquinone imine and
N-[[4'-N,N-(di-β-hydroxyethyl)amino]phenyl]-3-acetylamino-6-methyl benzoquinone imine.

Of these solutions, those in ethyl alcohol or in monoethyl ether of ethylene glycol are those which are more particularly preferred.

In the storage stable dye solutions of this invention, it is also possible to use a mixture of the above defined solvents and in association therewith one or more of the previously defined dyes. These storage stable dye solutions can also contain other dyes conventionally employed in the dyeing of hair, such as azo, anthraquinone and nitrobenzene dyes as well as 2,5-diamino benzoquinones and aryl azo pyridine N-oxides.

The indoaniline and/or indophenol dyes are generally present in these storage stable dye solutions in an amount between 0.001 and 5 weight percent and preferably between 0.002 and 1 weight percent thereof. The concentration of the dye can, of course, be adjusted depending, for instance, on the desired ultimate shade resulting from the application of the said solutions to the hair. It will be noted that by thus proceeding, it is possible to use dyes which are slowly or difficultly soluble in conventionally employed cosmetic vehicles or carriers. Further this procedure permits the use of high dye concentrations.

The process of improving the storage stability characteristics of these indoaniline and indophenol dyes, and hence preserving their dyeing power, comprises dissolving said dye in an anhydrous solvent as defined above, the dye being present in the above-indicated amounts.

The dyes stored in the said solvents retain their dyeing power for a period clearly longer than heretofore has been possible when the same dyes were stored in aqueous based hair dye compositions ready to be applied to the hair.

In another embodiment of the present invention, a hair dye composition for immediate application to the hair can be prepared by admixing a cosmetic vehicle conventionally employed in dyeing hair with a storage stable dye solution as defined above.

Thus, storage stable dye solutions of the present invention can be admixed with an aqueous based cosmetic carrier or vehicle to which has been added a sufficient amount of an alkalizing or acidifying agent so as to adjust the pH of the resulting hair dye composition to a value between 1 and 11 and preferably between 3 and 10.

The said aqueous based hair dye compositions can also include one or more of a solvent, a polymer, a cationic treating product, an amide, a thickening agent, a surface active agent or one or more adjuvants conventionally employed in capillary cosmetic compositions such as a solar filter, an optical bluing agent, an anti-oxidant, a sequesterant or a perfume.

These aqueous based hair dye compositions can also contain an oxidizing agent.

Representative alkalinizing agents include mono- or tri-ethanol amine, ammonia, sodium phosphate or sodium carbonate; representative acidifying agents include phosphoric acid, hydrochloric acid, lactic acid, tartaric acid, acetic acid or citric acid. The pH adjusting agents are destined to regulate the pH of the hair dye composition to the values indicated above.

Representative solvents usefully employed in the hair dye composition include low molecular weight alcohols, having 1-4 carbon atoms such as ethyl alcohol or isopropyl alcohol or glycols such as the monomethyl, monoethyl or monobutyl ether of ethylene glycol, propylene glycol and the monoethyl ether of diethylene glycol. The said solvent is present in an amount between 0.5 and 50, and preferably between 1 and 15, weight percent of the said hair dye composition.

Representative cosmetic polymers include polyvinylpyrrolidone having a molecular weight of 10,000 to 360,000; copolymers of 10% crotonic acid and 90% vinyl acetate, having a molecular weight of 10,000 to 70,000; copolymers of vinyl pyrrolidone (VP) and vinyl acetate (VA) having a molecular weight of 30,000 to 200,000, the VP/VA ratio being from 30/70 to 70/30; cationic polymers such as polymers of quaternized polyvinylpyrrolidone, quaternized cellulose derivatives, copolymers of N-vinylpyrrolidone and dimethylaminoethyl methacrylate and polyethylene glycol, quaternized with dimethyl sulfate, crosslinked or not.

The cosmetic polymers or resins are employed in an amount between 0.1 to 3 weight percent and preferably between 0.3 and 2 weight percent.

Representative amides include mono- or diethanolamides of fatty acids, optionally oxyethylenated.

Representative thickening agents include cellulosic derivatives such as carboxymethyl cellulose, hydroxypropyl methyl cellulose and hydroxyethyl cellulose.

Representative surface active agents include anionic, cationic, non-ionic or amphoteric surfactants such as the sulfates, ether sulfates and sulfonates of fatty alcohols; fatty acids or alcohols optionally oxyethylenated; oxyethylenated alkyl phenols; amines; and quaternized ammonium salts such as trimethyl cetyl ammonium bromide and cetyl pyridinium bromide.

Representative other adjuvants include benzylidene camphor, as a solar filter; butyl hydroxy anisole; sodium bisulfite, as an antioxidizing agent; and ethylene diamine tetraacetic acid, as a complexing agent.

When employed, the oxidizing agent can be $H_2O_2$ and it can be present in an amount between 1 to 6% by weight of the hair dye composition. Urea peroxide or per salts such as ammonium persulfate can also be employed as the oxidizing agent.

The amount of the storage stable dye solution, containing the dyes of Formula I, relative to the cosmetic vehicle such as defined above, ranges between 1 and 80% and preferably between 5 and 50%. Further, the amount can vary depending upon the concentration of the dye of Formula I in the storage stable dye solution and on the strength or depth of the shade that is desired to be imparted to the hair. It will be noted that it is possible to employ dye concentrations clearly higher than previously possible and thus from this fact, obtain a stronger and wider range of hair shades.

The admixture of the storage stable dye solution and the aqueous based cosmetic vehicle can be produced in various ways using known devices such as those having two separated compartments, one of which contains the storage stable dye solution of this invention, the other containing the cosmetic vehicle.

A preferred embodiment of the present invention comprises using an aerosol device having two compartments, whereby the mixture of the solvent phase containing the said dyes with the aqueous phase constituting the cosmetic vehicle is effected by means of a valve. Representative propellants for use in these aerosols include nitrogen, nitrous oxide, volatile hydrocarbons such as butane, isobutane, propane or preferably the fluorinated hydrocarbons (sold under the name Freon), and particularly fluorochloro hydrocarbons such as dichlorodifluoromethane (Freon 12), dichlorotetrafluoromethane (Freon 114) and trichloromonofluoromethane (Freon 11). These propellants can be used alone or in combination. A particularly effective propellant combination is a mixture of Freon 114 and Freon 12 present in proportions varying from 40:60 to 80:20, respectively.

Other known devices can also be employed and include, for instance, the packaging means described in commonly owned French Pat. Nos. 1,557,740; 73 46537; 71 08902; 72 02321; and 76 05827.

Representative of these devices is a bottle provided with a tubular stopper having a slidable capsule for containing the storage stable dye solution prior to its admixture with the cosmetic vehicle at the interior of the bottle. Another useful device is a non-pressurized container provided with at least one distribution orifice on its exterior cover which is made of a deformable supple material. This exterior cover which has an elongated form encloses at least one sealed and breakable rigid tube. The cosmetic vehicle is confined in the space defined by the exterior of this breakable rigid tube and at the interior of the flexible cover while the storage stable dye solution of the present invention is confined within the breakable rigid tube.

Another example of means usefully employed with the present invention consists of a bottle within which is confined the cosmetic vehicle or carrier, the bottle having disposed at the interior of the neck thereof a lid covered container or jar fitted with the storage stable dye solution. The admixture of these components is effected in this instance by sliding a trocar, supportingly maintained by a flange at the extreme edge of the neck of the bottle, whereby the trocar perforates the lid and the bottom of the container.

The hair dye compositions, thus prepared, are then applied to the hair in accordance with such conventional procedures as rinsing or shampooing. Conveniently, the thus applied composition is permitted to remain in contact with the hair for a period of time ranging from about 3 to 30 minutes.

The use of the storage stable dye solution of the present invention in these or similar compartmented packages or containers provides numerous economic advantages. Further, the production of hair dye compositions containing these storage stable dye solutions and the implementation of procedures utilizing the same are clearly less onerous than previously employed compositions and procedures.

The following non-limiting examples are given to illustrate the present invention. Unless otherwise specified, all parts and percentages are by weight.

Examples of Cosmetic Vehicles or Carriers

The following examples illustrate various conventional cosmetic vehicles or carriers employed in hair dyeing operations. These cosmetic carriers are used in combination with the storage stable dye solutions of the present invention to provide a hair dye composition which is applied, immediately after its preparation, to the hair. Obviously conventional cosmetic carriers, other than those specifically set forth below, will occur to those skilled in this art and thus the present invention is not to be limited either by these specifically exemplified carriers or by the specific procedures employed in dyeing the hair.

Cosmetic Carrier A

Polyvinylpyrrolidone, M.W. 40,000—0.5 g
Trimethylcetylammonium bromide—0.2 g
Ethyl alcohol, sufficient for 12°5
Triethanolamine, sufficient for pH=7
Water, sufficient for—100 cc Cosmetic Carrier B Polyvinylpyrrolidone, M.W. 40,000—0.5 g
Trimethylcetylammonium bromide—0.2 g
GAFQUAT 734, in active material—0.4 g
Ethyl alcohol, sufficient for 37°5
Triethanolamine, sufficient for pH=7
Water, sufficient for—100 cc Cosmetic Carrier C Copolymer of vinyl acetate/crotonic acid (90/10), M.W. 45,000-50,000—2.0 g
Copolymer of vinyl acetate/vinylpyrrolidone, (40/60), sold under the name PVP/VA S630—0.38 g
Ethyl alcohol, sufficient for 37°5
Triethanolamine, sufficient for pH=7
Water, sufficient for—100 cc Cosmetic Carrier D Polyvinylpyrrolidone, M.W. 40,000—0.8 g
Trimethylcetylammonium bromide—0.2 g
Triethanolamine, sufficient for pH=7
Water, sufficient for—100 cc Cosmetic Carrier E Trimethylcetylammonium bromide—0.125 g
Copolymer of vinylpyrrolidone/vinyl acetate (60/40), sold under the name of PVP/VA S630—0.60 g
$H_2O_2$ (200 vol.) sufficient for—12.5 vol.
Orthophosphoric acid, sufficient for pH=3
Ethyl alcohol, sufficient for 37°5
Water, sufficient for—100 cc Cosmetic Carrier F Copolymer of vinylpyrrolidone/vinyl acetate, (70/30), M.W. 40,000—0.35 g
Trimethylcetylammonium bromide—0.1 g
Ethyl alcohol, sufficient for 33°
Triethanolamine, sufficient for pH=7
Water, sufficient for—100 cc Cosmetic Carrier G Copolymer of vinylpyrrolidone/vinyl acetate (60/40), sold under the name of PVP/VA S630—0.25 g
Monoethanolamine, sufficient for pH=9
Water, sufficient for—100 cc Cosmetic Carrier H Sodium lauryl ether sulfate (30% active material) sold under the mark Delf 8533—25.0 g
Butyl cellosolve—1.0 g
Copradiethanolamide—5.0 g
Citric acid, sufficient for pH=6
Water, sufficient for—100 cc Cosmetic Carrier I Trimethylcetylammonium bromide—5.0 g
Lauryl alcohol oxyethylenated with 12.5 moles of ethylene oxide sold under the mark FREPAL 12—4.0 g
Citric acid, sufficient for pH=4
Water, sufficient for—100 cc It will be noted that in cosmetic carriers A and C, the ethyl alcohol can be replaced by isopropyl alcohol in those instances where the storage stable dye solution contains isopropyl alcohol.

GAFQUAT 734 used in cosmetic carrier B is quaternary copolymer of polyvinylpyrrolidone having an average molecular weight lower than 100,000 and is provided in the form of a 50% solution in alcohol having a relative viscosity, Ostwald-Fenske, of 2.5-3.5.

Examples of Storage Stable Dye Solutions and Hair Dye Compositions Prepared Therefrom Table I below illustrates various storage stable dye solutions of the present invention. This Table contains information and data relating to the nature of the dyes employed, the amount in grams of each dye used, the nature of the solvent employed in preparing these solutions and the amount of solvent used.

Example 1

(a) After eight months of storage in a tight container, dye solution $S_1$ set forth in Table I is used to prepare a hair dye composition by mixing 5 cc of this storage stable solution at the moment of use with 20 cc of cosmetic carrier A defined above.

The resulting hair dye composition is applied to light chestnut colored hair. The hair, after drying, untangles easily and exhibits particularly luminous mahogany glints.

(b) After 4 months of storage in an ampoule, dye solution $S_1$, as defined in Table I, is released by breaking the ampoule and 5 cc of this storage stable solution are mixed with 20 cc of cosmetic carrier C. The resulting hair dye composition in the form of a hair setting lotion is then applied to blonde hair using conventional procedures. This hair setting lotion imparts to the hair particularly esthetic light coppery mahogany glints.

(c) By replacing, in the preceding example, cosmetic carrier C with cosmetic carrier E, and by using the same amount of the storage stable dye solution and carrier, and by applying the resulting hair dye composition by washing natural blonde hair, there is obtained, after drying, slightly brightened hair which is easily untangled and which exhibits very luminous mahogany glints.

(d) At the moment of use, 2.5 cc of solution $S_1$ previously stored for 2 months, is mixed with 22.5 cc of cosmetic carrier G. The resulting hair setting lotion is then applied to deep blonde hair, which after drying, exhibits particularly esthetic mahogany glints.

Examples 2-25

Table II below illustrates the use of the storage stable dye solutions defined in Table I, in the preparation of various types of hair dye compositions. Table II includes data relating to the nature of the storage stable dye solution employed, the duration of storage, the amount of the dye solution mixed with the selected cosmetic vehicle, the selected cosmetic vehicle and the amount thereof employed in admixture with the storage stable dye solution, the pH of the hair dye composition resulting from this admixture, the nature of the hair being dyed and the shade or coloration obtained. The mixture of the storage stable dye solution with the cosmetic carrier can be effected in accordance with conventional procedures, including those mentioned in Example 1. Additional means of effecting this admixture are described in commonly owned French Pat. Nos. 1,557,740; 73 46537; 71 08902; 72 02321; and 76 05827.

In carrying out the present invention, the hair dye compositions prepared with cosmetic carriers A, B, C, D, E, F and G are applied by a rinsing technique while the hair dye compositions prepared with cosmetic carriers H and I are applied as a shampoo.

Example 26

A hair dye composition is prepared using an aerosol container having two separated compartments. One of the compartments contains a storage stable dye solution of this invention; the other contains a conventional cosmetic carrier. These two solutions provide at the moment of use a 1:1 mixture thereof. The storage stable dye solution is solution $S_9$, set forth in Table I, while the cosmetic carrier employed is carrier D defined above. The storage stable dye solution and carrier are each present in an amount of 42.5 cc. 15 g of an aerosol propellant comprising a mixture of Freon 11 and Freon 12 in a weight ratio of 60/40 are admixed with the storage stable dye solution.

20 g of this hair dye composition are applied, using a rinsing technique, to hair having a light chestnut coloration. After drying, the hair untangles easily and exhibits particularly luminous mahogany glints.

Example 27

A hair dye composition is prepared using an aerosol container having two separated compartments, one of the compartments contains a storage stable dye solution of this invention, the other contains a conventional cosmetic carrier. These two solutions provide at the moment of use a 1:1 mixture thereof. The storage stable dye solution is solution $S_{10}$, set forth in Table I, while the cosmetic carrier is carrier D, defined above. Dye solution $S_{10}$ and carrier D are each present in an amount of 42.5 cc. 15 g of an aerosol propellant comprising a mixture of Freon 114 and Freon 12, in a weight ratio of 80/20, are mixed with the storage stable dye solution.

20 g of this hair dye composition using a conventional rinsing technique are applied to hair having a deep blonde coloration. After drying, the hair untangles easily and exhibits a beautiful, irridescent, deep blonde shade.

TABLE I

| Solution | Dyes | Amount (g) | Solvents | Amount (cc) |
|---|---|---|---|---|
| $S_1$ | N-[(4'-hydroxy-2'-chloro)phenyl] 3-acetylamino-2,6-dimethyl benzoquinone imine | 0.660 | Absolute ethyl alcohol | sufficient for 100 |
| | N-[(4'-hydroxy-2'-chloro)phenyl]-3-ureido-6-methyl benzoquinone imine | 0.130 | | |
| | N-[[4'-N,N(ethyl, carbamylmethyl) amino-2'-methyl]phenyl] 3-acetyl-amino-6-methyl benzoquinone imine | 0.018 | | |
| $S_2$ | N-[(4'-hydroxy-2'-chloro)phenyl] 3-acetylamino-2,6-dimethyl benzoquinone imine | 0.017 | | |
| | N-[(4'-hydroxy)phenyl]-2,6-dimethyl 3-acetylamino benzoquinone imine | 0.005 | | |
| | N-[(4'-hydroxy-2'-chloro)phenyl] 3-ureido-6 methyl benzoquinone imine | 0.002 | | |
| | N-[[4'-N,N(ethyl, mesylaminoethyl) amino-2'-methyl]phenyl] 3-amino-6 methyl benzoquinone imine | 0.066 | Absolute ethyl alcohol | sufficient for 100 |

TABLE I-continued

| Solution | Dyes | Amount (g) | Solvents | Amount (cc) |
|---|---|---|---|---|
| | 2-N-β-hydroxyethylamino-5-(4-di-β-hydroxy ethylamino anilino)-1,4-benzoquinone | 0.002 | | |
| S₃ | N-[(4'-hydroxy-2'-chloro)phenyl] 3-acetylamino-2,6-dimethyl benzoquinone imine | 0.090 | | |
| | N-[(4'-hydroxy-2'-chloro)phenyl] 3-acetylamino-6-methoxy benzoquinone imine | 0.008 | Absolute ethyl alcohol | sufficient for 100 |
| | N-[[4'-N,N(ethyl, carbamylmethyl) amino-2'-methyl]phenyl] 3-acetylamino-6-methyl benzoquinone imine | 0.015 | | |
| | 2-N-β-hydroxyethylamino-5-(4-di-β-hydroxy ethylamino anilino)-1,4-benzoquinone | 0.006 | | |
| S₄ | N-[(4'-hydroxy-2'-chloro)phenyl] 3-acetylamino-2,6-dimethyl benzoquinone imine | 0.115 | | |
| | N-[(4'-hydroxy)phenyl]-2,6-dimethyl-3-acetylamino benzoquinone imine | 0.085 | Absolute ethyl alcohol | sufficient for 100 |
| | N-[(4'-hydroxy-2'-chloro)phenyl] 3-ureido-6 methoxy benzoquinone imine | 0.360 | | |
| S₅ | N-[(4'-hydroxy-2'-chloro)phenyl] 3-acetylamino-2,6-dimethyl benzoquinone imine | 0.148 | | |
| | N-[(4'-hydroxy-2'-chloro)phenyl]-3-ureido-6 methyl benzoquinone imine | 0.005 | | |
| | N-[[4'N,N(ethyl, carbamylmethyl) amino-2'-methyl]phenyl]-3-acetylamino-6 methyl benzoquinone imine | 0.020 | Absolute ethyl alcohol | sufficient for 100 |
| | 2-N-β-hydroxyethylamino-5-(4-di-β-hydroxyethylamino anilino) 1,4-benzoquinone | 0.002 | | |
| S₆ | N-[4'-hydroxy-2'-chloro)phenyl] 3-ureido-6 methyl benzoquinone imine | 0.060 | sufficient for | |
| | N-[[4'-N,N(ethyl, mesylaminoethyl) amino-2'-methyl]phenyl] 3-amino-6-methyl benzoquinone imine | 0.119 | Absolute ethyl alcohol | 100 100 |
| S₇ | N-[(4'-hydroxy-2'-chloro)phenyl]-3-acetylamino-2,6-dimethyl benzoquinone imine | 0.600 | | |
| | N-[(4'-hydroxy-2'-chloro)phenyl]-3-ureido-6-methyl benzoquinone imine | 0.012 | | |
| | N-[[4'-N,N(ethyl, carbamylmethyl) amino-2'-methyl-2]phenyl]-3-acetylamino-6-methyl-6 benzoquinone imine | 0.012 | Absolute ethyl alcohol | sufficient for 100 |
| | 2-N-β-hydroxyethylamino-5-(4-di-β-hydroxy ethylamino- anilino)-1,4-benzoquinone | 0.008 | | |
| S₈ | N-[(4'-hydroxy-2'-chloro)phenyl]-3-ureido-6-methyl benzoquinone imine | 0.120 | | |
| | N-[[4'-N,N-(ethyl, mesylaminoethyl) amino-2'-methyl]phenyl]-3-amino-3-methyl benzoquinone imine | 0.238 | Absolute ethyl alcohol | sufficient for 100 |
| S₉ | N-[(4'-hydroxy-2-'-chloro)phenyl]-3-acetylamino-2,6-dimethyl benzoquinone imine | 0.660 | | |
| | N-[(4'-hydroxy-2'-chloro)phenyl]-3-ureido-6-methyl benzoquinone imine | 0.130 | Absolute ethyl alcohol | sufficient for 100 |
| | N-[[4'-N,N-(ethyl, carbamylmethyl) amino-2'-methyl]phenyl]-3-acetylamino-6-methyl benzoquinone imine | 0.018 | | |
| | N-[[4'-N,N-(ethyl, carbamylmethyl) amino]phenyl]-3-carbethoxyamino-6- | | | |

TABLE I-continued

| Solution | Dyes | Amount (g) | Solvents | Amount (cc) |
|---|---|---|---|---|
| | methoxy benzoquinone imine | 0.010 | | |
| S₁₀ | N-[(4'-hydroxy-2'-chloro)phenyl]-3-acetylamino-2,6-dimethyl benzoquinone imine | 0.148 | | |
| | N-[(4'-hydroxy-2'-chloro)phenyl]-3-ureido-6-methyl benzoquinone imine | 0.005 | | |
| | N-[[4'-N,N-(ethyl, carbamylmethyl) | | Absolute ethyl alcohol | sufficient for 100 |
| | N-[[4'-N,N-(ethyl, carbamylmethyl)amino-2'-methyl]phenyl]-3-acetylamino-6-methyl benzoquinone imine | 0.002 | | |
| | 2-N-β-hydroxyethylamino-5-(4-di-β-hydroxyethylamino anilino)-1,4-benzoquinone | 0.002 | | |
| S₁₁ | N-[(4'-hydroxy)phenyl]-2,6-dimethyl-3-acetylamino benzoquinone imine | 0.820 | | |
| | N-[(4'-hydroxy-2'-chloro)phenyl]-3-ureido-6-methyl benzoquinone imine | 0.220 | | |
| | N-[(4'-amino)phenyl]-2,6-dimethyl-3-acetylamino benzoquinone imine | 0.064 | Monoethyl ether of ethylene glycol | sufficient for 100 |
| | 2-N-β-hydroxyethylamino-5-(2-methoxy-4-amino anilino)-1,4-benzoquinone | 0.088 | | |
| S₁₂ | N-[(4'-amino)phenyl]-2,6-dimethyl-3-acetylamino benzoquinone imine | 0.238 | | |
| | N-[(4'-hydroxy-2'-chloro)phenyl]-3-ureido-6-methyl benzoquinone imine | 0.006 | | |
| | N-[(4'-hydroxy-2'-chloro)phenyl]-3-acetylamino-2,6-dimethyl benzoquinone imine | 0.007 | Monoethyl ether of ethylene glycol | sufficient for 100 |
| | 2-N-β-hydroxyethylamino-5 (2-methoxy-4-amino anilino)-1,4-benzoquinone | 0.120 | | |
| S₁₃ | N-[4'-amino-2'-methoxy-3',5'-dimethyl)phenyl]-3-acetylamino-6-methyl benzoquinone imine | 0.190 | | |
| | N[4'-amino)phenyl]-2,6-dimethyl-3-acetylamino benzoquinone imine | 0.105 | Monoethyl ether of ethylene glycol | sufficient for 100 |
| | N-[4'-hydroxy)phenyl]-3-acetylamino-6-methyl benzoquinone imine | 0.013 | | |
| S₁₄ | N-[(4'-hydroxy)phenyl]-3-amino-6-methyl benzoquinone imine | 0.35 | | |
| | N-[(4'-hydroxy-2'-chloro)phenyl]-2,6-dimethyl benzoquinone imine | 0.35 | | |
| | 2-N-β-hydroxyethylamino-5-(2-methoxy-4-amino-5-methyl anilino)-1,4-benzoquinone | 0.30 | Monoethyl ether of ethylene glycol | sufficient for 100 |
| S₁₅ | N-[(4'-methylamino-3'-chloro)phenyl]-3-acetylamino-2,6-dimethyl benzoquinone imine | 0.040 | Ethyl alcohol | sufficient for 100 |
| S₁₆ | N-[(4'-hydroxy-2'-chloro)phenyl]-3-acetylamino-2,6-dimethyl benzoquinone imine | 0.40 | | |
| | N-[(4'-hydroxy-2'-methyl)phenyl]-3-amino-2,6-dimethyl benzoquinone imine | 0.10 | | |
| | N-[[4'-N,N(ethyl, carbamylmethyl)amino]phenyl]-3-amino-2,6-dimethyl benzoquinone imine | 0.05 | Ethyl alcohol | sufficient for 100 |
| | N-[(4'-amino-2',5'-dimethyl)phenyl]-3-ureido-6-methyl benzoquinone imine | 0.02 | | |
| | N-[(4'-amino-3'-chloro)phenyl]-3-acetylamino-2,6-dimethyl benzoquinone imine | 0.001 | | |
| S₁₇ | N-[[4'-N,N(ethyl, mesylaminoethyl)amino-2'-methyl]phenyl]-2,5-dimethyl benzoquinone imine | 0.075 | | |
| | N-[(4'-hydroxy-2'-chloro)phenyl]-3-acetylamino-2,6-dimethyl benzoquinone imine | 0.10 | | |
| | N-[(4'-ethylamino-3'-chloro)phenyl]-3-acetylamino-6-methyl | | Isopropyl alcohol | sufficient for 100 |

TABLE I-continued

| Solution | Dyes | Amount (g) | Solvents | Amount (cc) |
|---|---|---|---|---|
| | benzoquinone imine | 0.05 | | |
| | 2-N-β-hydroxyethylamino-5 (4-di-β-hydroxyethylamino anilino)-1,4-benzoquinone | 0.030 | | |
| $S_{18}$ | N-[(4'-hydroxy-2'-chloro)phenyl]-3-acetylamino-2,6-dimethyl benzoquinone imine | 0.25 | Isopropyl alcohol | sufficient for 100 |
| | N-[(4'-hydroxy-2'-chloro)phenyl]-2-methyl-5-ureido benzoquinone imine | 0.10 | | |
| | N-[(4'-amino-2',6'-dimethyl-3'-methoxy)phenyl]-3-acetylamino-2,6-dimethyl benzoquinone imine | 0.03 | | |
| $S_{19}$ | N-[(4'-methylamino-3'-chloro)phenyl]-3-ureido-6-methyl benzoquinone imine | 0.10 | Tert. butyl alcohol | sufficient for 100 |
| | N-[(4'-dimethylamino-3'-chloro)phenyl]-3-amino-6-methyl benzoquinone imine | 0.005 | | |
| | N-[[4'-N,N(ethyl, carbamylmethyl)amino-2'-methyl]phenyl]-3-ureido-6-methyl benzoquinone imine | 0.01 | | |
| $S_{20}$ | N-[(4'-amino-2',6'-dimethyl-3'-methoxy)phenyl]-3-amino-6-methyl benzoquinone imine | 0.10 | Monomethyl ether of ethylene glycol | sufficient for 100 |
| | N-[[4'-N,N(ethyl, carbamylmethyl)amino]phenyl]-3-acetylamino-2,6-dimethyl benzoquinone imine | 0.20 | | |
| | N-[(4'-hydroxy-3'-methyl)phenyl]-3-amino-6-methyl benzoquinone imine | 0.01 | | |
| | 4'-phenylamino-1':2 benzene azo-3-methyl pyridine N-oxide | 0.01 | | |
| $S_{21}$ | N-[[4'-N,N(ethyl, carbamylmethyl)amino]phenyl]-3-ureido-6-methyl benzoquinone imine | 0.10 | Monomethyl ether of ethylene glycol | sufficient for 100 |
| | N-[[4'-N,N(ethyl, carbamylmethyl)amino]phenyl]-3-carbethoxyamino-6-methyl-benzoquinone imine | 0.15 | | |
| | N-[(4'-hydroxy-2'-chloro)phenyl]-3-acetylamino-2,6-dimethyl benzoquinone imine | 0.01 | | |
| | 4'-dimethylamino-1':2 benzene azo-3-methyl pyridine N-oxide | 0.01 | | |
| | 2-N-β-hydroxyethylamino-5 (4-di-β-hydroxyethylamino anilino)-1,4-benzoquinone | 0.15 | | |
| $S_{22}$ | N-[(4'-di-β-hydroxyethylamino)phenyl]-3-acetylamino-6-methyl benzoquinone imine | 0.02 | Monobutyl ether of ethylene glycol | sufficient for 100 |
| | N-[(4'-dimethylamino-2'-methyl)phenyl]-3-acetylamino-6-methyl benzoquinone imine | 0.01 | | |
| | N-[(4'-hydroxy-2'-chloro)phenyl]-3-acetylamino-2,6-dimethyl benzoquinone imine | 0.50 | | |
| | N[(4'-dimethylamino-3'-chloro)phenyl]-3-amino-6-methyl benzoquinone imine | 0.15 | | |
| $S_{23}$ | N-[[4'-N,N(ethyl, mesylaminoethyl)amino]phenyl]-3-acetylamino-2,6-dimethyl benzoquinone imine | 0.15 | Monobutyl ether of ethylene glycol | sufficient for 100 |
| | N-[[4'-N,N(ethyl, carbamylethyl)amino-2'-methyl]phenyl]-3-ureido-6-methyl-6 benzoquinone imine | 0.05 | | |
| | N-[(4'-hydroxy-2'-chloro)phenyl]-3-acetylamino-2,6-dimethyl benzoquinone imine | 0.01 | | |
| $S_{24}$ | N-[(4'-hydroxy-2'-chloro)phenyl]-3-acetylamino-2,6-dimethyl benzoquinone imine | 3.00 | Monomethyl ether of ethylene glycol | sufficient for 100 |
| $S_{25}$ | N-[[4'-N,N(ethyl, carbamylmethyl)amino]phenyl]-2,6-dimethyl benzoquinone imine | 1.00 | Monomethyl ether of ethylene glycol | sufficient for 100 |

TABLE I-continued

| Solution | Dyes | Amount (g) | Solvents | Amount (cc) |
|---|---|---|---|---|
| $S_{26}$ | N-[(4'-hydroxy-2'-chloro)phenyl]-3-acetylamino-2,6-dimethyl benzoquinone imine | 0.135 | | |
| | N-[(4'-hydroxy)phenyl]-2,6-dimethyl 3-acetylamino benzoquinone imine | 0.450 | | |
| | N-[(4'-hydroxy-2'-chloro)phenyl] 6-methyl-3-ureido benzoquinone imine | 0.400 | Absolute ethyl alcohol | sufficient for 100 |
| | N-[[4'-N,N-(ethyl, mesylaminoethyl) amino]phenyl]-3-acetylamino-2,6-dimethyl benzoquinone imine | 0.100 | | |
| | 2-N-β-hydroxyethylamino-5-(4-ethyl, β-acetylaminoethyl anilino)-1,4-benzoquinone | 0.430 | | |
| $S_{27}$ | N-[(4'-hydroxy-3'-chloro)phenyl]-3-acetylamino-6-methoxy benzoquinone imine | 0.05 | Monoethyl ether of ethylene glycol | sufficient for 100 |
| | N-[(4'-β-hydroxyethylamino-3'-chloro)phenyl]-3-ureido-6-methyl benzoquinone imine | 0.1 | | |
| | N-[(4'-hydroxy-2'-chloro)phenyl]-3-acetylamino-2,6-dimethyl benzoquinone imine | 0.3 | | |
| | N-[(4'-hydroxy-2'-chloro)phenyl]-3-ureido-6-methyl benzoquinone imine | 0.1 | | |

TABLE II

| Examples | Solution Nature | Duration of Storage | Amount (cc) | Cosmetic Vehicle Nature | Amount (cc) | pH Composition | Nature of Hair Being Dyed | Color of Hair After Treatment |
|---|---|---|---|---|---|---|---|---|
| $E_2$ | $S_2$ | 12 months | 5 | A | 20 | 7 | light blonde | light ash blonde |
| | $S_2$ | 4 months | 5 | E | 20 | 3 | light blonde | light ash blonde |
| $E_3$ | $S_3$ | 15 months | 5 | A | 20 | 7 | bleached | beige |
| $E_4$ | $S_4$ | 4 months | 5 | B | 20 | 7 | deep blonde | light coppery mahogany glints |
| $E_5$ | $S_5$ | 1 month | 5 | B | 20 | 7 | very light blonde | very luminous and very light irridescent blonde |
| | $S_5$ | 1 month | 5 | C | 20 | 7 | very light blonde | very luminous and very light irridescent blonde |
| | $S_5$ | 1 month | 10 | D | 10 | 7 | deep blonde | irridescent deep blonde |
| $E_6$ | $S_6$ | 5 months | 10 | D | 10 | 7 | deep blonde | deep ash blonde |
| | $S_6$ | 5 months | 2.5 | G | 22.5 | 9 | blonde | very luminous ash blonde |
| $E_7$ | $S_7$ | 10 months | 1 | G | 19 | 9 | very light blonde | very luminous pink glints |
| $E_8$ | $S_8$ | 24 months | 1 | G | 19 | 9 | deep blonde | deep ash blonde |
| $E_9$ | $S_{11}$ | 6 months | 2.5 | F | 22.5 | 7 | light chestnut | coppery mahogany light chestnut |
| $E_{10}$ | $S_{12}$ | 17 months | 2.5 | F | 22.5 | 7 | blonde | very luminous ash blonde |
| $E_{11}$ | $S_{13}$ | 8 days | 2.5 | B | 22.5 | 7 | 80% white | beautiful light gray glints |
| $E_{12}$ | $S_{14}$ | 3 months | 2.5 | F | 22.5 | 7 | light blonde | light golden blonde |
| $E_{13}$ | $S_{15}$ | 14 months | 2.5 | F | 22.5 | 7 | very light blonde | very luminous, very light ash blonde |
| $E_{14}$ | $S_{16}$ | 9 months | 5 | A | 20 | 7 | light chestnut | very luminous mahogany glints |
| | $S_{16}$ | 9 months | 5 | C | 20 | 7 | blonde | mahogany glints |
| $E_{15}$ | $S_{17}$ | 1 month | 5 | A | 20 | 7 | deep blonde | deep ash blonde |
| | $S_{17}$ | 1 month | 5 | C | 20 | 7 | light blonde | very luminous ashen glints |
| $E_{16}$ | $S_{18}$ | 15 months | 5 | A | 20 | 7 | light blonde | coppery mahogany glints |
| | $S_{18}$ | 15 months | 5 | C | 20 | 7 | very light blonde | very luminous pink glints |
| $E_{17}$ | $S_{19}$ | 9 months | 5 | A | 20 | 7 | natural blonde | very luminous violet glints |
| | $S_{19}$ | 9 months | 5 | C | 20 | 7 | blonde | irridescent blonde |
| $E_{18}$ | $S_{20}$ | 4 months | 2.5 | F | 22.5 | 7 | light blonde | light ash blonde |
| | $S_{20}$ | 4 months | 2.5 | G | 22.5 | 9 | deep blonde | irridescent ashen glints |

TABLE II-continued

| Examples | Solution Nature | Duration of Storage | Amount (cc) | Cosmetic Vehicle Nature | Amount (cc) | pH Composition | Nature of Hair Being Dyed | Color of Hair After Treatment |
|---|---|---|---|---|---|---|---|---|
| $E_{19}$ | $S_{21}$ | 12 months | 2.5 | F | 22.5 | 7 | blonde | ash blonde |
|  | $S_{21}$ | 12 months | 2.5 | G | 22.5 | 9 | gray | bluish gray |
| $E_{20}$ | $S_{22}$ | 17 months | 2.5 | F | 22.5 | 7 | light blonde | pink glints |
|  | $S_{22}$ | 17 months | 2.5 | G | 22.5 | 9 | chestnut | mahogany glints |
| $E_{21}$ | $S_{23}$ | 6 months | 2.5 | F | 22.5 | 7 | deep blonde | ashen glints |
|  | $S_{23}$ | 6 months | 2.5 | G | 22.5 | 9 | natural blonde | beautiful ashen glints |
| $E_{22}$ | $S_{24}$ | 10 months | 1 | H | 19 | 6 | bleached | very luminous pearly glints |
| $E_{23}$ | $S_{25}$ | 20 months | 1 | I | 19 | 4 | very light blonde | ashen glints (after contact time of 15 min.) |
| $E_{24}$ | $S_{26}$ | 12 months | 2.5 | H | 22.5 | 7 | bleached | beige (after contact time of 15 min.) |
| $E_{25}$ | $S_{27}$ | 13 months | 2.5 | F | 22.5 | 7 | light blonde | very luminous pearly light blonde |

What is claimed is:

1. A process for improving the storage stability of a dye having the formula:

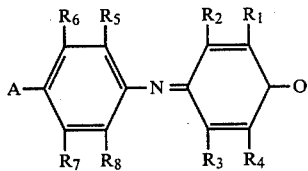

and selected from the group consisting of (1) a dye wherein

A is selected from the group consisting of hydroxy and

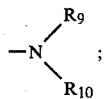

$R_1$, $R_2$, $R_3$ and $R_4$ are selected from the following groups of values:

(a) $R_1$ is methyl, $R_2$ is hydrogen, $R_3$ is methyl and $R_4$ is hydrogen,
(b) $R_1$ is methyl, $R_2$ is hydrogen, $R_3$ is hydrogen and $R_4$ is methyl,
(c) $R_1$ is methyl, $R_2$ is hydrogen, $R_3$ is amino and $R_4$ is hydrogen,
(d) $R_1$ is methyl, $R_2$ is hydrogen, $R_3$ is amino and $R_4$ is methyl,
(e) $R_1$ is methyl, $R_2$ is hydrogen, $R_3$ is acetylamino and $R_4$ is hydrogen,
(f) $R_1$ is methyl, $R_2$ is hydrogen, $R_3$ is acetylamino and $R_4$ is methyl,
(g) $R_1$ is methyl, $R_2$ is hydrogen, $R_3$ is carbamylamino and $R_4$ is hydrogen, and
(h) $R_1$ is methoxy, $R_2$ is hydrogen, $R_3$ is acetylamino and $R_4$ is hydrogen; with the proviso that when A is hydroxy, $R_5$, $R_6$, $R_7$ and $R_8$ are selected from the following groups of values:

(i) $R_5$, $R_6$, $R_7$ and $R_8$ are each hydrogen,
(j) $R_5$ is chlorine and $R_6$, $R_7$ and $R_8$ are each hydrogen,
(k) $R_5$ is methyl and $R_6$, $R_7$ and $R_8$ are each hydrogen,
(l) $R_5$ is hydrogen, $R_6$ is chlorine and $R_7$ and $R_8$ are each hydrogen, and
(m) $R_5$ is hydrogen, $R_6$ is methyl and $R_7$ and $R_8$ are each hydrogen; and that when A is

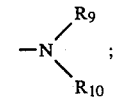

$R_5$, $R_6$, $R_7$, $R_8$, $R_9$ and $R_{10}$ are selected from the following group of values:

(n) $R_5$ is hydrogen, $R_6$ is chlorine and $R_7$, $R_8$, $R_9$ and $R_{10}$ are each hydrogen,
(o) $R_5$ is hydrogen, $R_6$ is chlorine, $R_7$, $R_8$ and $R_9$ are each hydrogen and $R_{10}$ is ethyl,
(p) $R_5$ is hydrogen, $R_6$ is chlorine, $R_7$, $R_8$ and $R_9$ are each hydrogen and $R_{10}$ is hydroxyethyl,
(q) $R_5$, $R_6$, $R_7$ and $R_8$ are each hydrogen and $R_9$ and $R_{10}$ are each hydroxyethyl,
(r) $R_5$ is methyl, $R_6$, $R_7$ and $R_8$ are each hydrogen and $R_9$ and $R_{10}$ are each methyl,
(s) $R_5$ is methyl, $R_6$, $R_7$ and $R_8$ are each hydrogen, $R_9$ is ethyl and $R_{10}$ is carbamylmethyl,
(t) $R_5$ is methyl, $R_6$, $R_7$ and $R_8$ are each hydrogen, $R_9$ is ethyl and $R_{10}$ is mesylamino ethyl, and
(u) $R_5$ is hydrogen, $R_6$ is chlorine, $R_7$ and $R_8$ are each hydrogen and $R_9$ and $R_{10}$ are each methyl;

(2) a dye wherein

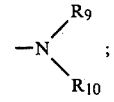

$R_1$, $R_2$, $R_3$ and $R_4$ are selected from the following groups of values:

(a) $R_1$ is methyl, $R_2$ is hydrogen, $R_3$ is amino and $R_4$ is hydrogen or methyl,
(b) $R_1$ is methyl, $R_2$ is hydrogen, $R_3$ is acetylamino and $R_4$ is methyl,
(c) $R_1$ is methyl, $R_2$ is hydrogen, $R_3$ is carbamylamino and $R_4$ is hydrogen, and
(d) $R_1$ is methoxy, $R_2$ is hydrogen, $R_3$ is acetylamino and $R_4$ is hydrogen; and $R_5$, $R_6$, $R_7$, $R_8$, $R_9$ and $R_{10}$ are selected from the following group of values:

(e) $R_5$ is methyl, $R_6$ is methoxy, $R_7$ is hydrogen, $R_8$ is methyl, $R_9$ is hydrogen and $R_{10}$ is hydrogen, and (f) $R_5$ is hydrogen, $R_6$ is methyl, $R_7$ is hydrogen, $R_8$ is methyl, $R_9$ is hydrogen and $R_{10}$ is hydrogen;

(3) a dye wherein A is

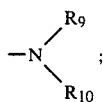

$R_1$, $R_2$, $R_3$ and $R_4$ are selected from the following groups of values:

(a) $R_1$ is methyl, $R_2$ is hydrogen, $R_3$ is methyl and $R_4$ is hydrogen, (b) $R_1$ is methyl, $R_2$ is hydrogen, $R_3$ is hydrogen and $R_4$ is methyl, (c) $R_1$ is methyl, $R_2$ is hydrogen, $R_3$ is amino and $R_4$ is hydrogen, (d) $R_1$ is methyl, $R_2$ is hydrogen, $R_3$ is amino and $R_4$ is methyl, (e) $R_1$ is methyl, $R_2$ is hydrogen, $R_3$ is acetylamino and $R_4$ is methyl, (f) $R_1$ is methyl, $R_2$ is hydrogen, $R_3$ is carbamylamino and $R_4$ is hydrogen, and (g) $R_1$ is methoxy, $R_2$ is hydrogen, $R_3$ is acetylamino and $R_4$ is hydrogen; and $R_5$, $R_6$, $R_7$, $R_8$, $R_9$ and $R_{10}$ are selected from the following groups of values:

(h) $R_5$ is hydrogen, $R_6$ is chloro, $R_7$ is hydrogen, $R_8$ is hydrogen, $R_9$ is hydrogen and $R_{10}$ is methyl, (i) $R_5$, $R_6$, $R_7$, and $R_8$ are hydrogen, $R_9$ is ethyl and $R_{10}$ is carbamylmethyl and (j) $R_5$, $R_6$, $R_7$ and $R_8$ are hydrogen, $R_9$ is ethyl and $R_{10}$ is mesylaminoethyl; and (4) a dye wherein A is

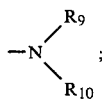

$R_1$ is methyl, $R_2$ is hydrogen, $R_3$ is carbethoxy amino, $R_4$ is hydrogen, and $R_5$, $R_6$, $R_7$, $R_8$, $R_9$ and $R_{10}$ are selected from the following groups of values:

(a) $R_5$, $R_6$, $R_7$ and $R_8$ are each hydrogen and $R_9$ and $R_{10}$ are each hydroxyethyl, (b) $R_5$ is methyl, $R_6$, $R_7$ and $R_8$ are each hydrogen and $R_9$ and $R_{10}$ are each methyl, (c) $R_5$ is hydrogen, $R_6$ is chlorine, $R_7$ and $R_8$ are each hydrogen and $R_9$ and $R_{10}$ are each methyl, (d) $R_5$ is methyl, $R_6$, $R_7$ and $R_8$ are each hydrogen, $R_9$ is ethyl and $R_{10}$ is carbamylmethyl, (e) $R_5$, $R_6$, $R_7$ and $R_8$ are each hydrogen, $R_9$ is ethyl and $R_{10}$ is carbamylmethyl, (f) $R_5$ is methyl, $R_6$, $R_7$ and $R_8$ are each hydrogen, $R_9$ is ethyl and $R_{10}$ is mesylamino ethyl, and (g) $R_5$, $R_6$, $R_7$ and $R_8$ are each hydrogen, $R_9$ is ethyl and $R_{10}$ is mesylaminoethyl, comprising dissolving at least one said dye in an anhydrous solvent selected from the group consisting of ethyl alcohol, isopropyl alcohol, tertiary butyl alcohol, monoethyl ether of ethylene glycol, monomethyl ether of ethylene glycol, monobutyl ether of ethylene glycol and their mixtures, wherein a solution is formed which contains 0.001 to 5 weight percent of said dye, and maintaining said dye in the presence of said anhydrous solvent during the storage thereof.

2. The process of claim 1 wherein said dye has the formula as defined in (1).

3. The process of claim 1 where in said dye A is

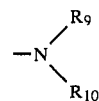

and $R_1$, $R_2$, $R_3$ and $R_4$ are selected from the following groups of values:

(a) $R_1$ is methyl, $R_2$ is hydrogen, $R_3$ is amino and $R_4$ is hydrogen or methyl, (b) $R_1$ is methyl, $R_2$ is hydrogen, $R_3$ is acetylamino and $R_4$ is methyl, (c) $R_1$ is methyl, $R_2$ is hydrogen, $R_3$ is carbamylamino and $R_4$ is hydrogen, and (d) $R_1$ is methoxy, $R_2$ is hydrogen, $R_3$ is acetylamino and $R_4$ is hydrogen; and $R_5$, $R_6$, $R_7$, $R_8$, $R_9$ and $R_{10}$ are selected from the following group of values:

(e) $R_5$ is methyl, $R_6$ is methoxy, $R_7$ is hydrogen, $R_8$ is methyl, $R_9$ is hydrogen and $R_{10}$ is hydrogen, and (f) $R_5$ is hydrogen, $R_6$ is methyl, $R_7$ is hydrogen, $R_8$ is methyl, $R_9$ is hydrogen and $R_{10}$ is hydrogen.

4. The process of claim 1 where in said dye A is

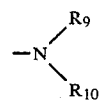

and $R_1$, $R_2$, $R_3$ and $R_4$ are selected from the following group of values:

(a) $R_1$ is methyl, $R_2$ is hydrogen, $R_3$ is methyl and $R_4$ is hydrogen, (b) $R_1$ is methyl, $R_2$ is hydrogen, $R_3$ is hydrogen and $R_4$ is methyl, (c) $R_1$ is methyl, $R_2$ is hydrogen, $R_3$ is amino and $R_4$ is hydrogen, (d) $R_1$ is methyl, $R_2$ is hydrogen, $R_3$ is amino and $R_4$ is methyl, (e) $R_1$ is methyl, $R_2$ is hydrogen, $R_3$ is acetylamino and $R_4$ is methyl, (f) $R_1$ is methyl, $R_2$ is hydrogen, $R_3$ is carbamylamino and $R_4$ is hydrogen, and (g) $R_1$ is methoxy, $R_2$ is hydrogen, $R_3$ is acetylamino and $R_4$ is hydrogen; and $R_5$, $R_6$, $R_7$, $R_8$, $R_9$ and $R_{10}$ are selected from the following groups of values:

(h) $R_5$ is hydrogen, $R_6$ is chloro, $R_7$ is hydrogen, $R_8$ is hydrogen, $R_9$ is hydrogen and $R_{10}$ is methyl, (i) $R_5$, $R_6$, $R_7$ and $R_8$ are hydrogen, $R_9$ is ethyl and $R_{10}$ is carbamylmethyl, and (j) $R_5$, $R_6$, $R_7$ and $R_8$ are hydrogen, $R_9$ is ethyl and $R_{10}$ is mesylaminoethyl.

5. The process of claim 1 where in said dye A is

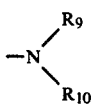

and
- $R_1$ is methyl,
- $R_2$ is hydrogen,
- $R_3$ is carbethoxy amino,
- $R_4$ is hydrogen, and
- $R_5$, $R_6$, $R_7$, $R_8$, $R_9$ and $R_{10}$ are selected from the following groups of values:
  - (a) $R_5$, $R_6$, $R_7$ and $R_8$ are each hydrogen and $R_9$ and $R_{10}$ are each hydroxyethyl,
  - (b) $R_5$ is methyl, $R_6$, $R_7$ and $R_8$ are each hydrogen and $R_9$ and $R_{10}$ are each methyl,
  - (c) $R_5$ is hydrogen, $R_6$ is chlorine, $R_7$ and $R_8$ are each hydrogen and $R_9$ and $R_{10}$ are each methyl,
  - (d) $R_5$ is methyl, $R_6$, $R_7$ and $R_8$ are each hydrogen, $R_9$ is ethyl and $R_{10}$ is carbamylmethyl,
  - (e) $R_5$, $R_6$, $R_7$ and $R_8$ are each hydrogen, $R_9$ is ethyl and $R_{10}$ is carbamylmethyl,
  - (f) $R_5$ is methyl, $R_6$, $R_7$ and $R_8$ are each hydrogen, $R_9$ is ethyl and $R_{10}$ is mesylamino ethyl, and
  - (g) $R_5$, $R_6$, $R_7$ and $R_8$ are each hydrogen, $R_9$ is ethyl and $R_{10}$ is mesylaminoethyl.

6. A process for improving the storage stability of a dye selected from the group consisting of:

N-[(4'-amino-3'-methoxy-2', 6'-dimethyl)phenyl]-2,6-dimethyl-3-acetylamino benzoquinone imine,
N-[(4'-β-hydroxyethylamino-3'-chloro)phenyl]-6-methyl-3-ureido benzoquinone imine,
N-[[4'-N,N-(ethyl, carbamylmethyl)amino]phenyl]-6-methyl-3-carbethoxyamino benzoquinone imine,
N-[(4'-methylamino-3'-chloro)phenyl]-6-methyl-3-ureido benzoquinone imine,
N-[(4'-methylamino-3'-chloro)phenyl]-2,6-dimethyl-3-acetylamino benzoquinone imine,
N-[(4'-hydroxy-2'-chloro)phenyl]-2,6-dimethyl-3-acetylamino benzoquinone imine,
N-[(4'-hydroxy-2'-chloro)phenyl]-6-methyl-3-ureido benzoquinone imine,
N-[[4'-N,N-(ethyl, carbamylmethyl)amino-2'-methyl]phenyl]-6-methyl-3-acetylamino benzoquinone imine,
N-[[4'-N,N-(ethyl, carbamylmethyl)amino-2'-methyl]phenyl]-6-methyl-3-ureido benzoquinone imine,
N-[[4'-N,N-(ethyl, carbamylmethyl)amino]phenyl]-2,6-dimethyl-3-acetylamino benzoquinone imine,
N-[(4'-amino-3'-chloro)phenyl]-2,6-dimethyl-3-acetylamino benzoquinone imine,
N-[(4'-amino-3',6'-dimethyl)phenyl]-6-methyl-3-ureido benzoquinone imine,
N-[[4'-N,N-(ethyl, mesylamino ethyl)amino-2'-methyl]phenyl]-3-amino-6-methyl benzoquinone imine,
N-[[4'-N,N-(ethyl, mesylamino ethyl)amino]phenyl]-2,6-dimethyl-3-acetylamino benzoquinone imine,
N-[(4'-hydroxy)phenyl]-3-acetylamino-6-methyl benzoquinone imine,
N-[(4'-amino-3'-chloro)phenyl]-3-acetylamino-6-methoxy benzoquinone imine,
N-[(4'-hydroxy)phenyl]-3-amino-6-methyl benzoquinone imine,
N-[[4'-N,N-(ethyl, carbamylmethyl)amino]phenyl]-3-carbethoxyamino-6-methoxy benzoquinone imine,
N-[(4'-hydroxy-2'-chloro)phenyl]-3-ureido-6-methoxy benzoquinone imine,
N-[(4'-hydroxy-2'-chloro)phenyl]-3-acetylamino-6-methoxy benzoquinone imine,
N-[[4'-N,N-(ethyl, carbamylmethyl)amino]phenyl]-3-ureido-6-methyl benzoquinone imine,
N-[[4'-N,N-(ethyl, carbamylmethyl)amino]phenyl]-3-acetylamino-6-methoxy benzoquinone imine,
N-[(4'-hydroxy)phenyl]-3-acetylamino-2,6-dimethyl benzoquinone imine,
N-[[4'-N,N-(di-β-hydroxyethyl)amino]phenyl]-3-acetylamino-6-methyl benzoquinone imine,
N-[(4'-methylamino-3'-chloro)phenyl]-3-ureido-6-methoxy benzoquinone imine, and
N-[[4'-N,N-(ethyl, carbamylmethyl)amino-3'-methyl]phenyl]-3-carbethoxyamino-6-methoxy benzoquinone imine, comprising dissolving at least one said dye in an anhydrous solvent selected from the group consisting of ethyl alcohol, isopropyl alcohol, tertiary butyl alcohol, monoethyl ether of ethylene glycol, monomethyl ether of ethylene glycol, monobutyl ether of ethylene glycol and their mixtures, wherein a solution is formed which contains 0.001 to 5 weight percent of said dye, and maintaining said dye in the presence of said anhydrous solvent during the storage thereof.

7. The process of claim 1 where said solution contains 0.002 to 1 weight percent of said dye.

8. The process of claim 1 wherein said solution also contains an azo dye, an anthraquinone dye, a nitrobenzene dye, a 1,5-diaminobenzoquinone or an aryl azo pyridine N-oxide.